United States Patent
Ng

(10) Patent No.: US 7,361,147 B2
(45) Date of Patent: Apr. 22, 2008

(54) NONINVASIVE BLOOD PRESSURE MONITORING SYSTEM

(75) Inventor: Kim-Gau Ng, Singapore (SG)

(73) Assignee: Healthstats International PTE Ltd, Singapore (SG)

(*) Notice: Subject to any disclaimer, the term of this patent is extended or adjusted under 35 U.S.C. 154(b) by 0 days.

(21) Appl. No.: 11/601,014

(22) Filed: Nov. 16, 2006

(65) Prior Publication Data

US 2007/0073163 A1   Mar. 29, 2007

Related U.S. Application Data

(62) Division of application No. 10/376,655, filed on Feb. 27, 2003, now Pat. No. 7,144,372.

(30) Foreign Application Priority Data

Jan. 29, 2003 (SG) .............................. 200300218-5

(51) Int. Cl.
 *A61B 5/02* (2006.01)
 *G01L 27/00* (2006.01)
(52) U.S. Cl. ........................................ 600/485; 702/98
(58) Field of Classification Search ................... 702/98
 See application file for complete search history.

(56) References Cited

U.S. PATENT DOCUMENTS

| | | | |
|---|---|---|---|
| 4,705,047 A | 11/1987 | Bailey | |
| 4,718,428 A | 1/1988 | Russell | |
| 5,163,438 A | 11/1992 | Gordon et al. | |
| 5,568,815 A | 10/1996 | Raynes et al. | |
| 6,471,646 B1 * | 10/2002 | Thede | 600/301 |
| 6,585,660 B2 | 7/2003 | Dorando et al. | |
| 2002/0173724 A1 * | 11/2002 | Dorando et al. | 600/486 |
| 2003/0141916 A1 * | 7/2003 | Conero | 327/291 |

FOREIGN PATENT DOCUMENTS

WO   WO 03-065633   8/2003

* cited by examiner

*Primary Examiner*—Charles A. Marmor, II
*Assistant Examiner*—Patricia Mallari
(74) *Attorney, Agent, or Firm*—Harness, Dickey & Pierce, P.L.C.

(57) ABSTRACT

The preferred embodiment of the present invention comprises a single microprocessor-based interface that connects between a noninvasive blood pressure (NIBP) sensor and an invasive blood pressure (IBP) monitor or module. The interface effectively emulates an IBP transducer in such a way that the IBP monitor sees the interface as if it were a regular IBP transducer from a fluid-filled blood pressure monitoring line. It receives the signal from an NIBP sensor and determines the blood pressure corresponding to the signal. It accepts the excitation voltage provided by the IBP monitor. From the excitation voltage and a known transducer sensitivity which the IBP monitor is configured to work with, the interface emulates the IBP transducer output signal corresponding to the blood pressure. The interface also emulates the input and output impedances of the IBP transducer which the IBP monitor is configured to work with. Zeroing of the interface with the IBP monitor can be easily performed in a way that is similar to that for a fluid-filled system. A noninvasive system comprising a suitable NIBP sensor and this interface can be used as an alternative to the fluid-filled monitoring line.

6 Claims, 14 Drawing Sheets

NONINVASIVE BLOOD PRESSURE MONITORING SYSTEM

CROSS REFERENCE TO RELATED APPLICATION

This application is a division of, and claims the benefit under 35 U.S.C. § 121 of U.S. patent application Ser. No. 10/376,655 (now U.S. Pat. No. 7,144,372), filed on Feb. 27, 2003.

FIELD OF INVENTION

The present invention relates to blood pressure monitoring, particularly but not solely to an interface between a noninvasive blood pressure sensor and an invasive blood pressure monitor.

BACKGROUND ART

Blood pressure is one of the most important vital signs used in the assessment of a patient's cardiovascular health. In critical care, it is usually monitored continuously using an invasive fluid-filled monitoring line, also called an arterial line, in which a catheter is inserted into an artery and blood pressure from the artery is transmitted to a blood pressure transducer through fluid-filled tubing 12 to 84 inches long. The arterial pressure as measured by the transducer is displayed on an invasive blood pressure (IBP) monitor. A schematic diagram of such a system is depicted in FIG. 1.

This intra-arterial method not only allows arterial pressure to be monitored continuously on a beat-to-beat basis, but also allows arterial blood to be sampled through the fluid-filled system without the need to cannulate another arterial site. In many hospitals, IBP monitors form part of a central monitoring system in which arterial pressure measurements from patients at various locations in the hospital can be monitored from a central location or from other locations in the hospital. However, this invasive method of monitoring blood pressure is associated with risks of complications such as infection, thrombosis and air embolism.

Noninvasive measurement methods that provide continuous beat-to-beat blood pressure offers an alternative to invasive blood pressure monitoring because they do not carry with them the risk of complications associated with invasive monitoring. The arterial tonometry and vascular unloading methods are two such methods. These methods can be used to measure blood pressure in situations that do not justify the use of invasive means, especially for patients who do not already have an arterial line in place and who also do not require arterial blood sampling.

Commercial noninvasive blood pressure (NIBP) monitors that provide continuous beat-to-beat measurement are mostly standalone monitors that not only cannot or cannot be easily connected to a central monitoring system, but also require a separate monitor to display their waveforms. For example, the Model 7000/CBM-7000 NIBP monitor and the Pilot/BP-508 multiparameter monitor by Colin (Komaki, Japan), both of which provide tonometric blood pressure measurement at the radial artery, are standalone monitors with their own displays and cannot be easily connected to a central monitoring system. The same applies to the Finapres® 2300 NIBP monitor and 2350 NIBP/SpO$_2$ monitors by Ohmeda (now Datex-Ohmeda, Madison, Wis., U.S.A.) and the USM-803 NIBP monitor by UEDA Electronic Works (Tokyo, Japan), all of which measure continuous beat-to-beat blood pressure at a finger using the vascular unloading method. A block diagram showing the main elements of such monitors is presented in FIG. 2.

Another commercial NIBP monitor, the Vasotrac® APM 205A by Medwave (Minneapolis, Minn., U.S.A.), measures blood pressure continually by providing one beat of the pressure waveform for approximately every 15 heartbeats, along with the corresponding systolic, diastolic and mean arterial pressure readings. It uses a modified oscillometric method in which various cycles of increasing and decreasing pressure are applied to the radial artery over a period of 15 heartbeats, and blood pressure is derived from the characteristics of the pressure signal detected by the sensor over this period of time. The main elements of this monitor are the same as those in FIG. 2.

The Vasotrac APM 205A is a standalone monitor. However, the company markets an optional interface, called the NIA V-Line, which connects the Vasotrac APM 205A to an existing IBP monitor to enable the pressure waveform to be displayed on the IBP monitor. A block diagram of an application of this interface is presented in FIG. 3. This interface is associated with U.S. Pat. No. 6,471,646 entitled ARTERIAL LINE EMULATOR. One drawback of this interface is that it requires the use of the Vasotrac itself in order for it to work, so a hospital that only wishes to display the NIBP waveform from the Vasotrac on its existing IBP monitors must purchase the Vasotrac in addition to the interface. This situation adds to the procurement costs for the hospital.

SUMMARY OF INVENTION

It is an object of the present invention to provide a device that goes some way toward overcoming the above disadvantages, or which will at least provide the public with a useful choice.

In a first aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to provide said output signal in a form suitable for input to an IBP monitor;

wherein said first input is connected to an NIBP sensor and said second input and said output are both connected to an IBP monitor.

Preferably said second input and said output are configured to connect to an IBP monitor by means of a detachable or configurable connection between said interface and an IBP interface cable for an IBP monitor.

Preferably said connection includes an adapter with a first connector configured to connect to said interface and a second connector configured to connect to the transducer end of an IBP interface cable.

Preferably said adapter includes a cable between said first and second connectors.

Preferably said adapter does not include a cable between said first and second connectors.

In a second aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to provide said output signal in a form suitable for input to an IBP monitor;

wherein said processor(s) is configured such that a user can select from a predetermined range of processing options.

Preferably said processor(s) comprises an embedded microprocessor system, a personal computer, or a combination of the two.

Preferably said processing options include an embedded microprocessor system, a personal computer, and a combination of the two.

Preferably said combination is configured such that said embedded microprocessor system and said personal computer work independently such that said interface can receive said measurement signal and said excitation signal and can generate an output signal indicative of the IBP of a subject according to predetermined instructions without said personal computer being used, and said personal computer forms an optional part of said interface and is used for additional signal and data processing.

Preferably said combination is configured such that both said embedded microprocessor system and said personal computer cooperate to receive said measurement signal and said excitation signal and to generate an output signal indicative of the IBP of a subject according to predetermined instructions.

In a third aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to provide said output signal in a form suitable for input to an IBP monitor;

wherein said processor(s) is configured such that a user can select the sensitivity of said output signal in relation to said measurement signal from a predetermined range of choices.

Preferably said sensitivity can be selected or specified by a user.

Preferably said range includes 5 µV/V/mmHg and 40 µV/V/mmHg.

In a fourth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor; configured to determine the differential voltage of said excitation signal; and configured to determine the midpoint voltage of said excitation signal;

at least one processor(s) configured to receive said measurement signal and said differential voltage and emulate an output signal indicative of the IBP of a subject according to predetermined instructions; and an output configured to receive said midpoint voltage and configured to provide said output signal in a form suitable for input to an IBP monitor; and such that the midpoint of said output signal is substantially similar to that of said midpoint voltage.

Preferably said second input includes a voltage divider, a differential amplifier, or a combination of the two configured to sense and condition said differential voltage.

Preferably said processor(s) is configured to receive both positive and negative ranges of said conditioned differential voltage through a circuit that includes an analog-to-digital converter (ADC).

Preferably said analog-to-digital converter (ADC) is a bipolar ADC.

Preferably said second input includes a voltage divider or a combination of a voltage divider and a differential amplifier, configured to sense and condition said midpoint voltage.

In a fifth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor; configured to determine the differential voltage of said excitation signal; and configured to determine the midpoint voltage of said excitation signal;

at least one processor(s) configured to receive said measurement signal, said differential voltage and said midpoint voltage and emulate an output signal indicative of the IBP of a subject according to predetermined instructions; and an output configured to provide said output signal in a form suitable for input to an IBP monitor; and such that the midpoint of said output signal is substantially similar to that of said midpoint voltage.

Preferably said second input includes a voltage divider, a differential amplifier, or a combination of the two, configured to sense and condition said differential voltage.

Preferably said processor(s) is configured to receive both positive and negative ranges of said conditioned differential voltage through a circuit that includes an analog-to-digital converter (ADC).

Preferably said analog-to-digital converter (ADC) is a bipolar ADC.

Preferably said second input includes a voltage divider or a combination of a voltage divider and a differential amplifier, configured to sense and condition said midpoint voltage.

Preferably said processor(s) is configured to receive both positive and negative ranges of said conditioned midpoint voltage through a circuit that includes an analog-to-digital converter (ADC).

Preferably said analog-to-digital converter (ADC) is a bipolar ADC.

Preferably said processor(s) includes a bipolar digital-to-analog converter (DAC) to provide said midpoint voltage to said output.

Preferably said output includes a voltage divider or a combination of a voltage divider and a differential amplifier, configured to scale and condition the output signal of said digital-to-analog converter (DAC) such that the midpoint voltage of the scaled and conditioned signal is substantially similar to said midpoint voltage.

In a sixth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and where the differential voltage of said output signal depends on said excitation signal, a predetermined or selectable transducer sensitivity, and said measurement signal; and an output configured to provide said output signal in a form suitable for input to said IBP monitors, including a digital-to-analog converter (DAC) to receive output signal from said processor(s), and said DAC is configured according to predetermined instructions such that its full-scale output voltage range includes the voltage range corresponding to a predetermined maximum pressure range of the NIBP of a subject.

Preferably said digital-to-analog converter (DAC) is a configurable bipolar DAC;

said processor(s) is further configured to configure said DAC; and said DAC is further configured to optimize the resolution of said full-scale output voltage range.

Preferably said full-scale voltage range is proportional to the result of the following mathematical expression:

$$V_{EXC} \times SENS \times (P_{MAX} - P_{MIN})$$

Preferably said output includes a circuit configured to scale and condition said output signal such that the differential voltage of said output signal is equal to the result of the following mathematical expression:

$$V_{EXC} \times SENS \times P$$

Preferably said circuit includes a voltage divider, a differential amplifier, or a combination of the two.

Preferably said processor(s) is further configured to increase the number of digital values for said output signal by interpolation so as to improve the smoothness of the signal that is input to an IBP monitor.

Preferably said interpolation includes linear interpolation, nonlinear interpolation, or a combination of the two.

In a seventh aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to determine the output differential voltage for said output signal; and having at least two terminals configured to provide said output signal in a form suitable for input to an IBP monitor;

wherein said second input, said processor(s) and said output are configured such that the voltage level of each of said two terminals is substantially similar to that produced by an IBP transducer for the same pressure variations in a subject.

Preferably said interface configured such that configured such that the output signal at said terminals is obtained by adding the midpoint voltage of said excitation signal with respect to the electrical ground of said interface, to the midpoint of said output differential voltage, this output differential voltage being the result of the following mathematical expression:

$$V_{EXC} \times SENS \times P$$

Preferably said output includes a summing amplifier to add the midpoint voltages.

Preferably said interface configured such that the output signal at said terminals is obtained by adding the midpoint voltage of said excitation signal with respect to the electrical ground of said interface, to the voltage at either terminal for said output differential voltage, this output differential voltage being the result of the following mathematical expression:

$$V_{EXC} \times SENS \times P$$

Preferably said output is configured such that said midpoint voltage of said excitation signal is added to the voltage at either terminal for said output differential voltage by a summing amplifier.

In an eighth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to provide said output signal in a form suitable for input to an IBP monitor;

wherein said second input is configured to provide an input impedance that is within a predetermined range.

Preferably said predetermined range is greater than 200 ohms.

Preferably said processor(s) and said second input are configured such that a user can select the input impedance.

Preferably said second input includes one or more resistors between the input terminals corresponding to said input impedance.

In a ninth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to provide said output signal in a form suitable for input to an IBP monitor;

wherein said output means is configured to provide an output impedance that is within a predetermined range.

Preferably said predetermined range is smaller than 3,000 ohms.

Preferably said processor(s) and said output are configured such that a user can select the output impedance.

Preferably said output includes one or more resistors placed across the output terminals corresponding to said output impedance.

In a tenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions;

an output configured to provide said output signal in a form suitable for input to an IBP monitor; and a calibration device configured to provide a calibration signal to said processor(s);

wherein said processor(s) is configured to calibrate said measurement signal according to predetermined instructions.

Preferably calibration of said measurement signal can be initiated and aborted by a user.

Preferably calibration of said measurement signal is automatically initiated and aborted by said processor(s) according to predetermined instructions.

Preferably calibration of said measurement signal is automatically initiated at predetermined intervals, at intervals that depend on deviations of said measurement signal from physiologically realistic signals, or at a combination of both groups of intervals.

In an eleventh aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor;

at least one processor(s) configured to receive said measurement signal and said excitation signal and emulate an output signal indicative of the IBP of a subject according to predetermined instructions; and an output configured to provide said output signal in a form suitable for input to an IBP monitor;

wherein said processor(s) is further configured to supply a zero signal to said output according to predetermined instructions.

Preferably said processor(s) is configured to supply said zero signal to said output when calibration of said measurement signal is in progress or when said measurement signal is distorted as a result of the calibration.

Preferably said processor(s) is configured to supply either said zero signal or said output signal to said output at any one time.

Preferably the sending of said zero signal and said output signal can be initiated and aborted by a user.

Preferably the sending of said zero signal and said output signal can be alternated by a user.

Preferably said zero signal is supplied to said output upon power-up of said interface.

Preferably said zero signal is always supplied to said output whenever no other signal is supplied to said output.

Preferably the output signal for said zero signal, is within ±75 mmHg.

In a twelfth aspect the present invention consists in a method of zeroing an interface configured to connect between a noninvasive blood pressure (NIBP) sensor and an invasive blood pressure (IBP) monitor comprising the steps of preparing said IBP monitor to receive said zero signal through an output, according to operating instructions for said IBP monitor;

sending said zero signal to said IBP monitor through said output;

zeroing on said IBP monitor, according to operating instructions for said IBP monitor; and preparing said IBP monitor to receive said NIBP measurement signal through said output, according to operating instructions for said IBP monitor.

In a thirteenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor; configured to determine the differential voltage of said excitation signal; and configured to determine the midpoint voltage of said excitation signal;

at least one processor(s) configured to receive said measurement signal and said differential voltage and emulate an output signal indicative of the IBP of a subject according to predetermined instructions;

an output configured to receive said midpoint voltage and configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the midpoint of said output differential voltage.

In a fourteenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor; configured to determine the differential voltage of said excitation signal; and configured to determine the midpoint voltage of said excitation signal;

at least one processor(s) configured to receive said measurement signal and said differential voltage and emulate an output signal indicative of the IBP of a subject according to predetermined instructions;

an output configured to receive said midpoint voltage and configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the voltage at either terminal for said output differential voltage.

In a fifteenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor; configured to determine the differential voltage of said excitation signal; and configured to determine the midpoint voltage of said excitation signal;

at least one processor(s) configured to receive said measurement signal, said differential voltage and said midpoint voltage and emulate an output signal indicative of the IBP of a subject according to predetermined instructions;

an output configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the midpoint of said output differential voltage.

In a sixteenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive a transducer excitation signal provided by an IBP monitor; configured to determine the differential voltage of said excitation signal; and configured to determine the midpoint voltage of said excitation signal;

at least one processor(s) configured to receive said measurement signal, said differential voltage and said midpoint voltage and emulate an output signal indicative of the IBP of a subject according to predetermined instructions;

an output configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the voltage at either terminal for said output differential voltage.

In a seventeenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive the differential voltage of an excitation signal provided by an IBP monitor; and configured to determine the midpoint voltage of said excitation signal;

at least one processor(s) configured to receive said measurement signal and said differential voltage and emulate an output signal indicative of the IBP of a subject according to predetermined instructions; and an output configured to receive said midpoint voltage and configured to provide said output signal in a form suitable for input to an IBP monitor; and such that the midpoint of said output signal is substantially similar to that of said midpoint voltage.

In a eighteenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive the differential voltage of an excitation signal provided by an IBP monitor; and configured to determine the midpoint voltage of said excitation signal;

at least one processor(s) configured to receive said measurement signal and said differential voltage and emulate an output signal indicative of the IBP of a subject according to predetermined instructions;

an output configured to receive said midpoint voltage and configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the midpoint of said output differential voltage.

In a nineteenth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive the differential voltage of an excitation signal provided by an IBP monitor; and configured to determine the midpoint voltage of said excitation signal;

at least one processor(s) configured to receive said measurement signal and said differential voltage and emulate an output signal indicative of the IBP of a subject according to predetermined instructions;

an output configured to receive said midpoint voltage and configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the voltage at either terminal for said output differential voltage.

In a twentieth aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive the differential voltage of the excitation signal provided by an IBP monitor; and configured to determine the midpoint voltage of said excitation signal;

at least one processor(s) configured to receive said measurement signal, said differential voltage and said midpoint voltage and emulate an output signal indicative of the IBP of a subject according to predetermined instructions; and an output configured to provide said output signal in a form suitable for input to an IBP monitor; and such that the midpoint of said output signal is substantially similar to that of said midpoint voltage.

In a twenty-first aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive the differential voltage of the excitation signal provided by an IBP monitor; and configured to determine the midpoint voltage of said excitation signal;

at least one processor(s) configured to receive said measurement signal, and said differential voltage and said midpoint voltage and emulate an output signal indicative of the IBP of a subject according to predetermined instructions;

an output configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the midpoint of said output differential voltage.

In a twenty-second aspect the present invention consists in an interface configured to connect between a noninvasive blood pressure (NIBP) sensor and an invasive blood pressure (IBP) monitor comprising a first input configured to receive a measurement signal indicative of the NIBP of a subject;

a second input configured to receive the differential voltage of the excitation signal provided by an IBP monitor; and configured to determine the midpoint voltage of said excitation signal;

at least one processor(s) configured to receive said measurement signal, said differential voltage and said midpoint voltage and emulate an output signal indicative of the IBP of a subject according to predetermined instructions;

an output configured to provide said output signal in a form suitable for input to an IBP monitor; and such that the midpoint of said output signal is substantially similar to that of said midpoint voltage;

said processor(s) and output are configured to provide an output differential voltage in relation to said measurement signal in a form suitable for input to an IBP monitor; and said output is configured to add said midpoint voltage to the voltage at either terminal for said output differential voltage.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of 0 which the following gives examples.

BRIEF DESCRIPTION OF DRAWINGS

One preferred form of the present invention will now be described with reference to the accompanying drawings in which.

DETAILED DESCRIPTION OF THE INVENTION

Figure 1:
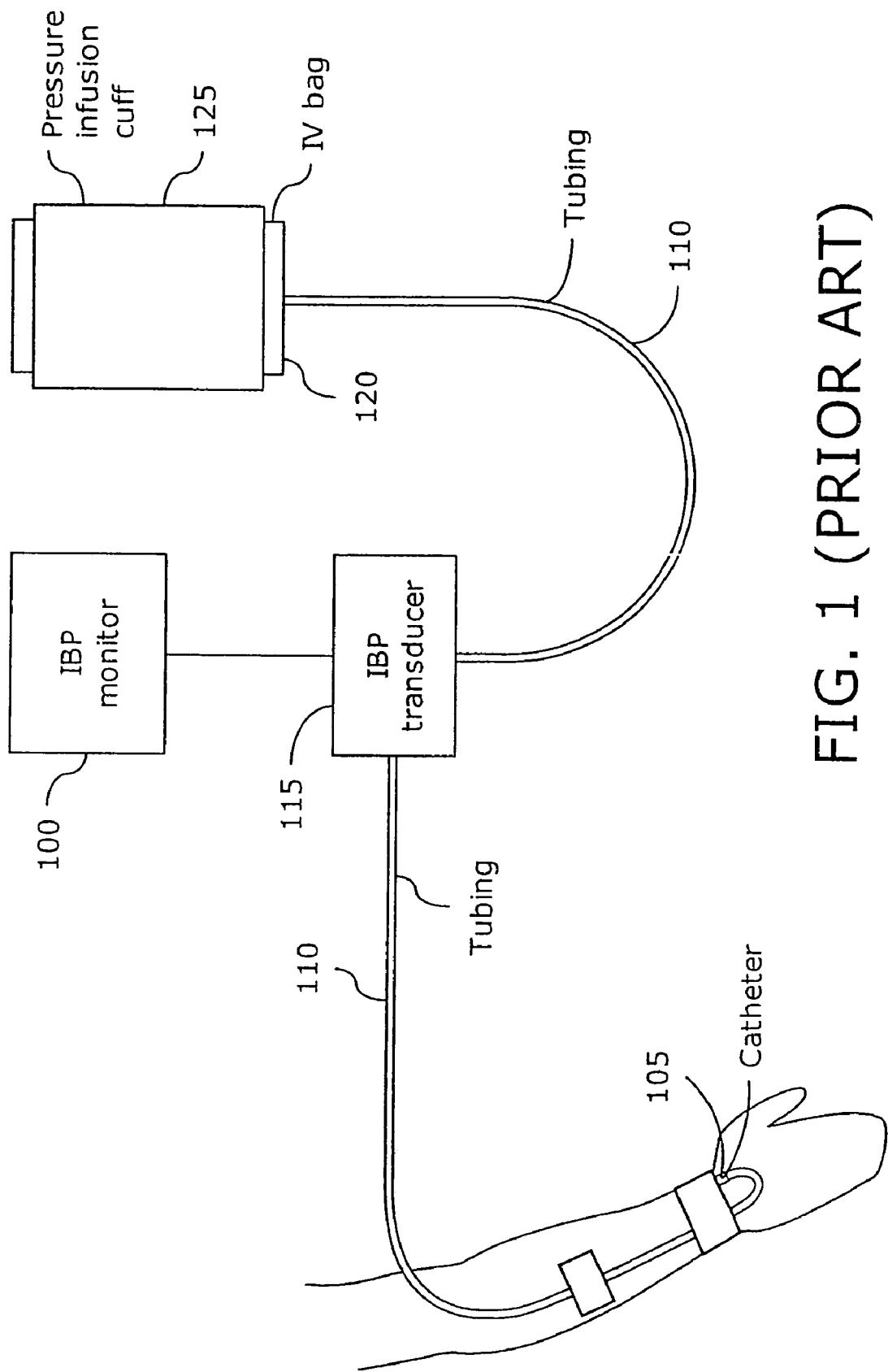
FIG. 1 is a schematic diagram of a prior art invasive blood pressure (IBP) monitoring system.
Figure 2:
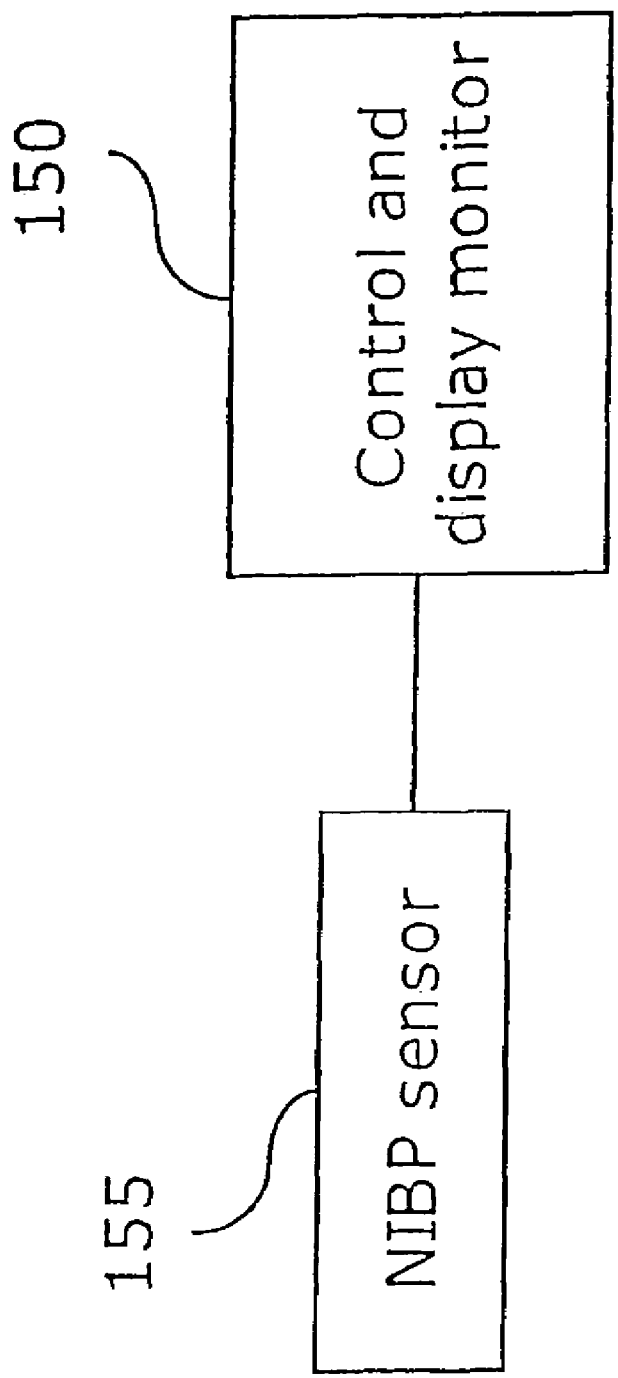
FIG. 2 is a block diagram of a prior art noninvasive blood pressure monitoring (NIBP) system comprising an NIBP sensor and a control and display monitor.
Figure 3:
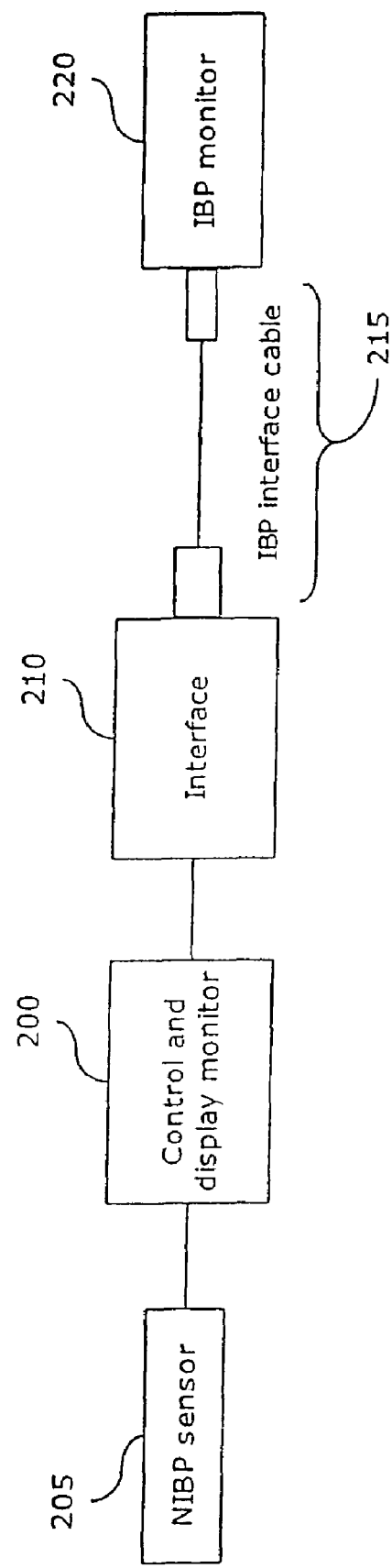
FIG. 3 is a block diagram of a prior art NIBP monitoring system comprising an NIBP sensor, a control and display monitor, and an interface.

An intra-arterial pressure or IBP monitoring system typically comprises a fluid-filled monitoring line (A-line) and an IBP monitor 100, as already depicted in FIG. 1. The fluid-filled monitoring line typically comprises a catheter 105, tubing 110, an IBP transducer 115 (also referred to simply as blood pressure transducer), an intravenous (IV) bag 120, and a pressure infusion cuff 125 for the IV bag 120. Most IBP transducers in use are usually either disposable or semi-disposable. A semi disposable transducer typically comprises a disposable dome that comes in contact with fluid in the system, and a reusable transducer that does not come in contact with the fluid. An electrical schematic of an IBP transducer is presented in FIG. 4.

An IBP interface cable is used to connect the transducer to the IBP monitor. The IBP monitor can come in the form of a standalone monitor, as part of an integrated multiparameter patient monitor, or as a plug-in module or cartridge of a modular multiparameter monitor. The present invention relates to the replacement of the fluid-filled monitoring line of an existing intra-arterial pressure monitoring system with a noninvasive system that is designed to work with the existing IBP monitor. The noninvasive system comprises an NIBP sensor, an interface, and if required, a calibrator to calibrate the NIBP measurement signal. The interface connects between the NIBP sensor and the IBP monitor.

The preferred embodiment of the present invention comprises a single microprocessor-based interface that connects a noninvasive blood pressure (NIBP) sensor to an invasive blood pressure (IBP) monitor or module. The interface effectively emulates an IBP transducer in such a way that the IBP monitor sees the interface as if it were a regular IBP transducer from a fluid-filled pressure monitoring line. It converts the blood pressure measured using an NIBP sensor into an equivalent IBP transducer output signal for input to an IBP monitor. Zeroing of the interface with the IBP monitor can be easily performed in a way that is similar to that for a fluid-filled system. A noninvasive system comprising a suitable NIBP sensor and this interface can be used as an alternative to the fluid-filled monitoring line.

The interface according to the present invention operates based on a known IBP transducer sensitivity, accepts the excitation voltage provided by the IBP monitor, and produces an equivalent IBP transducer output signal corresponding to the measured blood pressure. The interface also emulates the input and output impedances of the IBP transducer which the IBP monitor is configured to work with. The IBP monitor itself may be connected to a central monitoring system, but this connection may not be essential.

This interface offers the advantage of enabling continuous beat-to-beat blood pressure to be monitored by noninvasive means, while allowing the medical staff to continue to use existing IBP monitors which they are already familiar with. It allows medical staff to continue to benefit from multiparameter monitoring offered by patient monitors that provide monitoring of vitals signs such as ECG, oxygen saturation, respiration, and cardiac output, in addition to IBP. It also allows them to continue to benefit from the use of the central monitoring system to which the IBP or patient monitors are connected.

Figure 4:
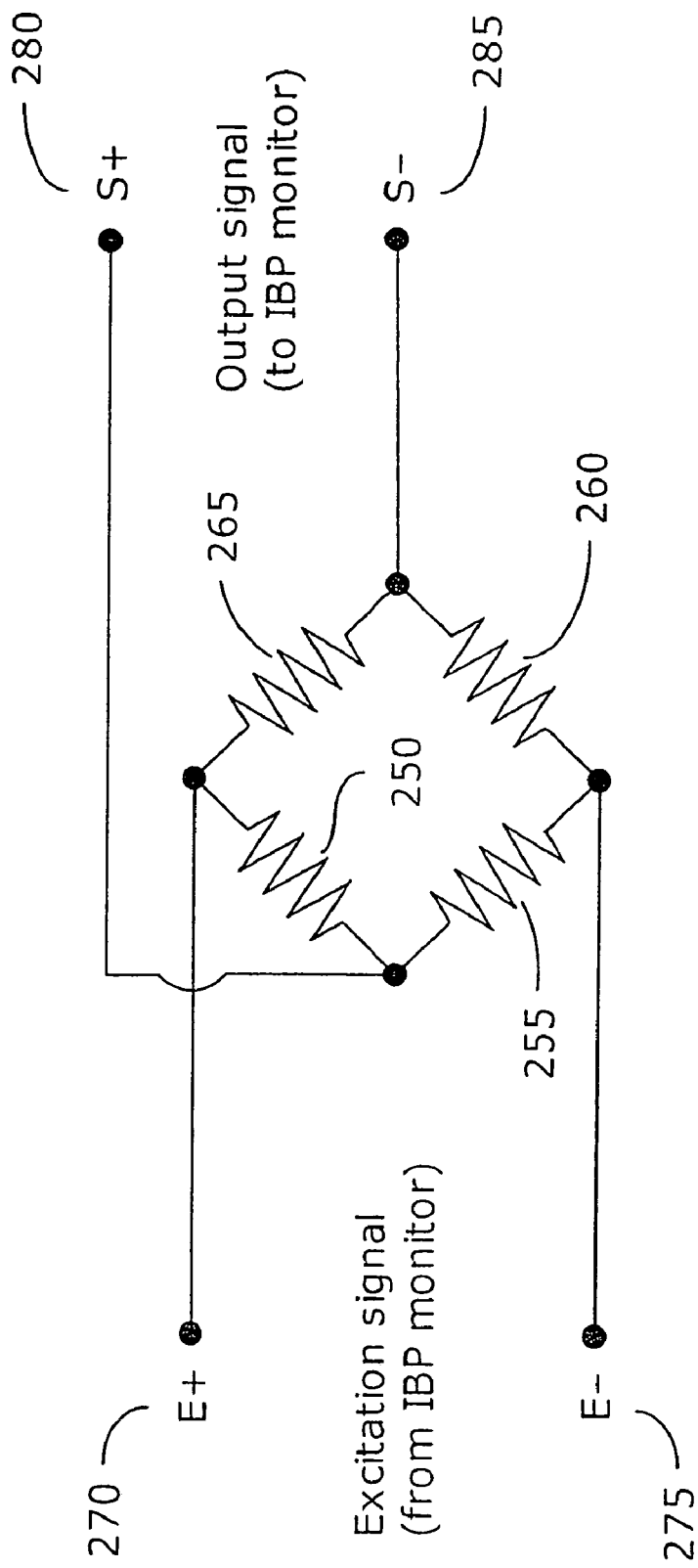
FIG. 4 is an electrical schematic diagram of a prior art invasive blood pressure transducer with a sensitivity of 5 µV/V/mmHg.

Characteristics of IBP Transducers Intended for Fluid-filled Blood Pressure Monitoring The sensor in most IBP transducers for fluid-filled monitoring consists of four sensing elements 250 255 260 265 of the same nominal resistance arranged in a full-bridge circuit, as illustrated in FIG. 4. The bridge has four terminals: E+ 270 and E− 275 for the input excitation voltage, and S+ 280 and S− 285 for the output signal. These four terminals are connected to the IBP monitor through a transducer cable and an IBP interface cable.

The two excitation voltage terminals receive the input excitation voltage supplied by the IBP monitor, while the two output signal terminals present to the IBP monitor the output voltage representing the blood pressure being measured. The nominal midpoint voltage of the output signal is the same as the midpoint voltage between the excitation terminals, this condition being the result of the sensing elements having the same nominal resistance. In other words, the midpoint of the differential output voltage is offset with respect to the negative excitation terminal E− by half the voltage across the excitation terminals. For example, if the voltage of the positive terminal E+ 270 with respect to the negative terminal E− is 5 V, the voltage across the output terminals S+ and S− will be such that the midpoint of this output voltage with respect to E− is 2.5 V.

Most IBP transducers in use conform to the ANSI/AAMI BP22-1994 standard for blood pressure transducers, accepting an excitation voltage of 4 to 8 VRM5 at a frequency of 0 to 5 kHz, and having a sensitivity of 5 µV/N/mmHg (5 µV output per volt of excitation voltage per mmHg of pressure), an input impedance greater than 200 ohms, an output impedance smaller than 3,000 ohms, and a zero balance within ±75 mmHg. At least one semi-disposable transducer, the HP 1290A by Hewlett Packard (later Agilent Healthcare, now Philips Medical Systems, Andover, Mass., U.S.A.), however, has a sensitivity of 40 µV/V/mmHg.

Emulation of IBP Transducers Intended for Fluid-filled Blood Pressure Monitoring The present invention relates to an interface that emulates an IBP transducer in such a way that that the IBP monitor sees the interface as if it were a regular IBP transducer from a fluid-filled pressure monitoring system. It senses the excitation voltage supplied by the monitor and for any given measured blood pressure, outputs an equivalent IBP transducer output signal to the IBP monitor, this signal being the same as the signal that would have been produced for that pressure by a transducer which the IBP monitor is configured to work with. For example, for a transducer sensitivity of 5 µV/V/mmHg, an excitation voltage of 5 V and a pressure of 100 mmHg, a IBP transducer will output a differential voltage of (5 µV/V/mmHg)×(5 V)×(100 mmHg), or 2.5 mV. For the same combination of sensitivity, excitation voltage and pressure, the interface will also output the same differential voltage of 2.5 mV. This differential voltage can be expressed algebraicly:

$$V_{EXC} \times SENS \times P$$

where $V_{EXC}$ is the root-mean-square (RMS) differential voltage across the excitation terminals, SENS is the transducer sensitivity which the IBP monitor is configured to work with, and P is the pressure measurement. The interface also emulates the input and output impedances of the transducer.

Single Interface Between NIBP Sensor and IBP Monitor

Figure 5:
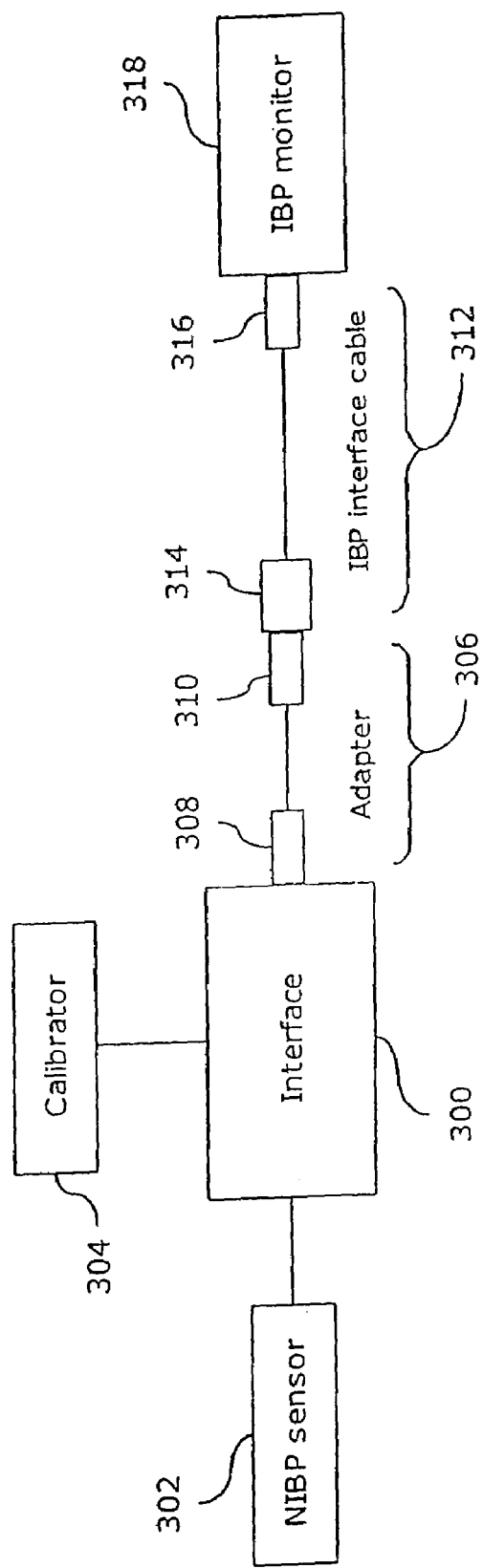
FIG. 5 is a block diagram of an NIBP monitoring system comprising an NIBP sensor, an interface, a calibrator, an adapter, an IBP interface cable, and an IBP monitor.

The present invention in one embodiment includes a single microprocessor-based interface that connects between an NIBP sensor and an IBP monitor. A block diagram of an NIBP monitoring system that comprises an NIBP sensor 302, an interface 300, a calibrator 304, an adapter 306, an IBP interface cable 312, and an IBP monitor 318 is presented in FIG. 5. The interface 300 connects to the IBP monitor 318 through the adapter 306 followed by the IBP interface cable 312. The adapter 306 and interface cable 312 each provides 4 wires to transmit the 4 signals corresponding to the four terminals E+, E−, S+ and S− of the IBP transducer. One end of the adapter 306 has a connector 308 that connects to the interface 300 and the other end has a connector 310 that connects to the IBP interface cable 312. The adapter may or may not include a cable between its two connectors.

In practice, the calibrator 304 may or may not be required, depending on whether the noninvasive method that is used for measuring blood pressure requires the NIBP measurement signal to be calibrated against blood pressure measurements made by another device. For example, the arterial tonometry method requires the NIBP measurement signal to be calibrated against blood pressure measurements made by another device, whereas the vascular unloading method does not. This is because the aerial tonometry method is not capable of establishing an absolute reference pressure level for its NIBP measurement signal, whereas the vascular unloading method has built-in calibration capability.

IBP interface cables are usually transducer-specific at the transducer end and monitor-specific at the IBP monitor's end, because different IBP transducers usually we different connector designs, as do different monitors. For example, an IBP interface cable that connects a Becton Dickinson (BD) (Franklin Lakes, N.J., U.S.A.) disposable transducer to a Hewlett-Packard (HP) IBP monitor (Philips Medical Systems) cannot be used to connect a Utah Medical Products (Midvale, Utah, U.S.A.) disposable transducer to the same monitor. The same IBP interface cable will not connect to a Datex-Ohmeda (Madison, Wis., U.S.A.) monitor. Although most IBP transducers use proprietary connectors, the telephone-type RJ11 plug (male part) is increasingly being used as a standard connector for disposable IBP transducers that are intended for fluid-filled, invasive blood pressure monitoring systems.

In order to connect the interface 300 to the IBP monitor 318, the interface-cable end of the adapter 306 must be designed in such a way that it can connect to the transducer end of the IBP interface cable 312. The interface-cable end of the adapter could be designed to accept take on the same connector as that on the cable of the transducer that is used with the IBP interface cable. A hospital that uses a particular brand of IBP transducers and a particular brand of IBP monitors would normally already have IBP interface cables for connecting the transducers to the monitors. The interface 300 can be designed to provide for the use of transducer-specific adapters, in that for every hospital that uses a different transducer, an adapter specific to that transducer is provided. This practice will enable the interface 100 to connect to existing IBP interface cables already in use, eliminating the need for hospitals to purchase a different interface cable.

Digital Processing

There are at least two approaches to the interface circuitry: the digital approach, and the analog approach. The digital approach uses a controller to perform, through software or firmware, the device control, data acquisition, digital signal processing and data processing, leaving the analog circuitry to perform signal conditioning. As a result of this, minimal analog circuitry is required, so that the cumulative analog signal level uncertainty caused by temperature changes is reduced. Although some uncertainty is introduced in the conversion of analog signal to digital signal and digital signal back to analog signal, this uncertainty is likely to be significantly smaller than that introduced by largely analog circuitry. One major advantage of the digital approach is that it offers the flexibility of allowing changes to device control, data acquisition, and signal and data processing to be easily implemented through software or firmware.

The analog approach uses largely analog circuitry to perform the necessary functions. Because of this, the analog circuitry is likely to be much more complex, so that the cumulative analog signal level uncertainty due to temperature changes is likely to be significantly greater than if the digital approach is used. Although the analog circuitry may not experience much error associated with analog-to-digital or digital-analog conversion, this advantage is likely to be overshadowed by the large signal uncertainty in the analog circuitry.

Figure 6:
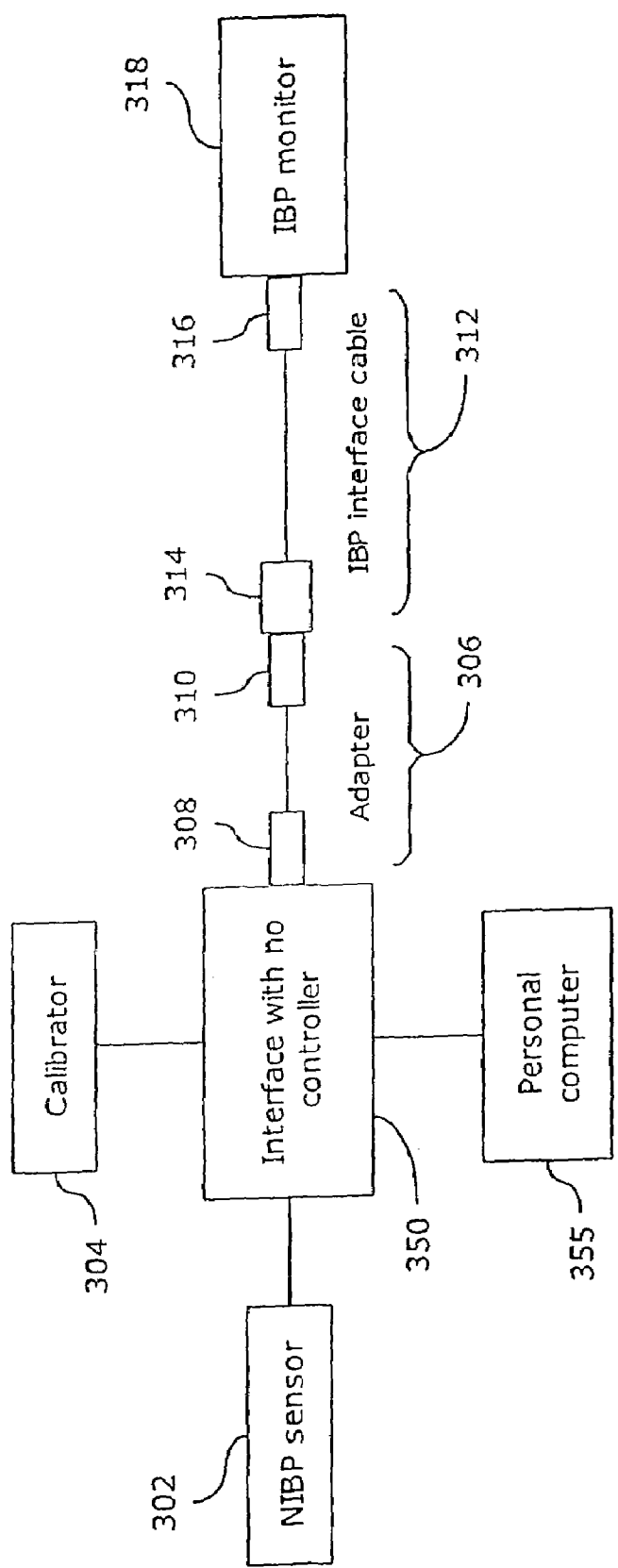
FIG. 6 is a block diagram of an embodiment of the NIBP monitoring system of FIG. 5 in which the interface uses a personal computer as the controller.

The present invention in the preferred embodiment uses the digital approach. At least three different design configurations are possible with the digital approach. The first configuration, as illustrated in FIG. 6, uses a personal computer (PC) 355 as the only controller. In this configuration, the PC 355 forms an essential part of the design and the interface 350 itself does not contain any controller. The PC 355 is used to perform, through software, extensive signal and data processing, both in real time and offline, as well as store the original and processed data. Although FIG. 6 rows that the calibrator 304 connects directly to the interface 350, the interface 350 an be designed to have the calibrator 304 connect directly to the PC 355 instead.

Figure 7:
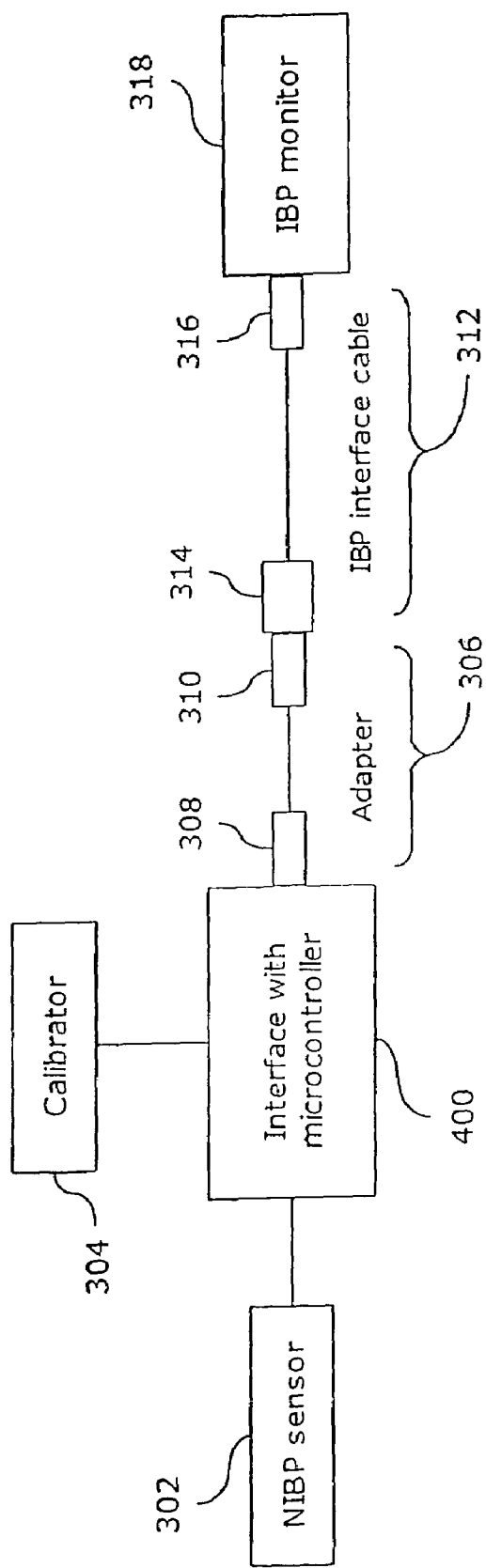
FIG. 7 is a block diagram of an embodiment of the NIBP monitoring system of FIG. 5 in which the interface uses a microcontroller as the controller.

The second configuration, as illustrated in FIG. 7, uses a microcontroller as the only controller. The microcontroller forms the central part of an embedded system. through firmware, it performs the same functions as those for the PC but in a limited way because of its lower processing power compared to a PC. The calibrator 304 connects to the interface 400.

Figure 8:
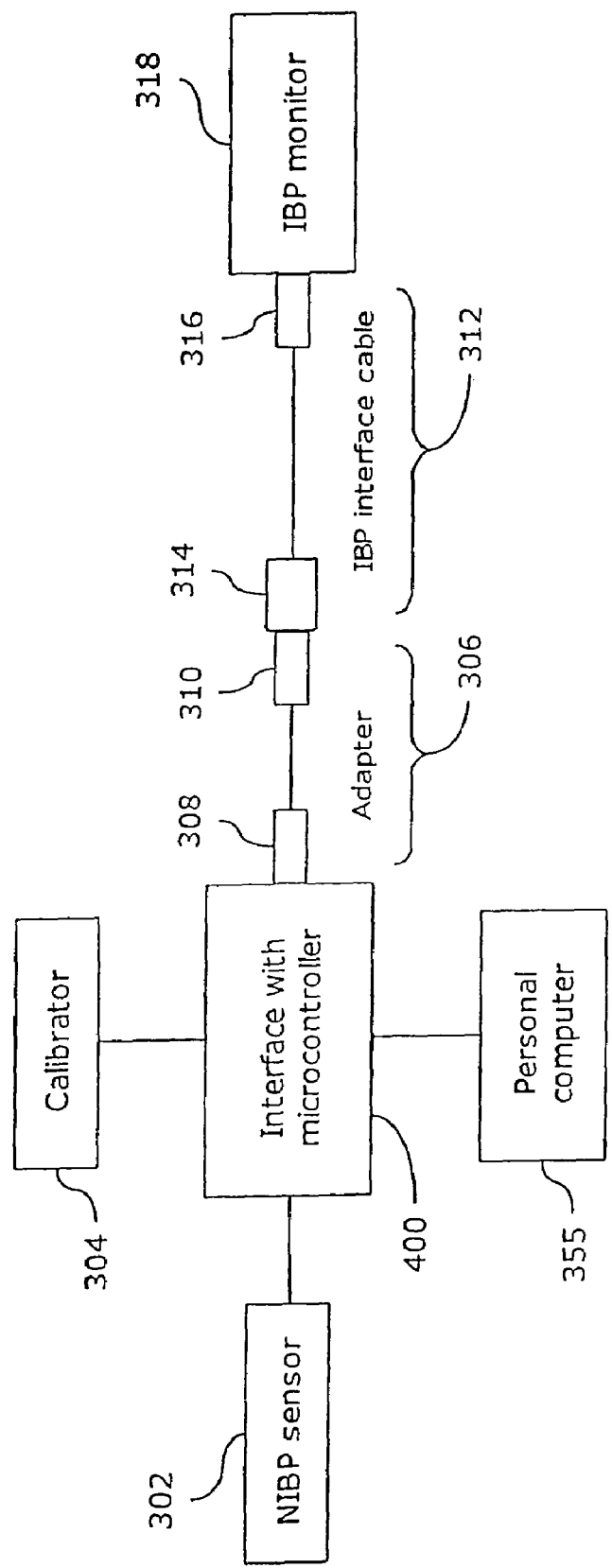
FIG. 8 is a block diagram of an embodiment of the NIBP monitoring system of FIG. 5 in which the interface works with both a personal computer and a microcontroller to accomplish the essential functions and more.

The third configuration, as illustrated in FIG. 8, uses a microcontroller as well as a PC 355. The microcontroller and PC 355 work together to accomplish the essential functions and more. Depending on the hardware, software and firmware configurations, there are many ways in which the microcontroller and PC 355 can work together to accomplish these functions. For example, the microcontroller and PC 355 could work independently in such a way that the microcontroller performs the same functions as in the second design configuration, while the PC 355 performs extensive signal and data processing to provide more information about the blood pressure measurement. In this example, the PC 355 is not an essential part of the design in that, without the PC 355, the interface 400 can still work with the IBP monitor 318. As another example, the microcontroller could perform the acquisition of the NIBP measurement signal and sending of digital values to the digital-to-analog converter (DAC), while the PC 355 works in between to perform extensive signal and data processing. In this configuration, both the microcontroller and PC 355 are essential parts of the design. Whether the calibrator 304 is connected to the interface 400 or to the PC 355 depends on the functions performed by the microcontroller and the PC 355. This configuration also allows the use of features that come with the PC 355, such as memory and data storage.

The interface can be designed to make all of above three configurations available and to allow the user to select any one of them through a control panel on the interface. In general, other user input, such as user-initiated calibration requests, can be effected through a control panel on the interface or though the PC.

General Operation of Interface

Figure 9:
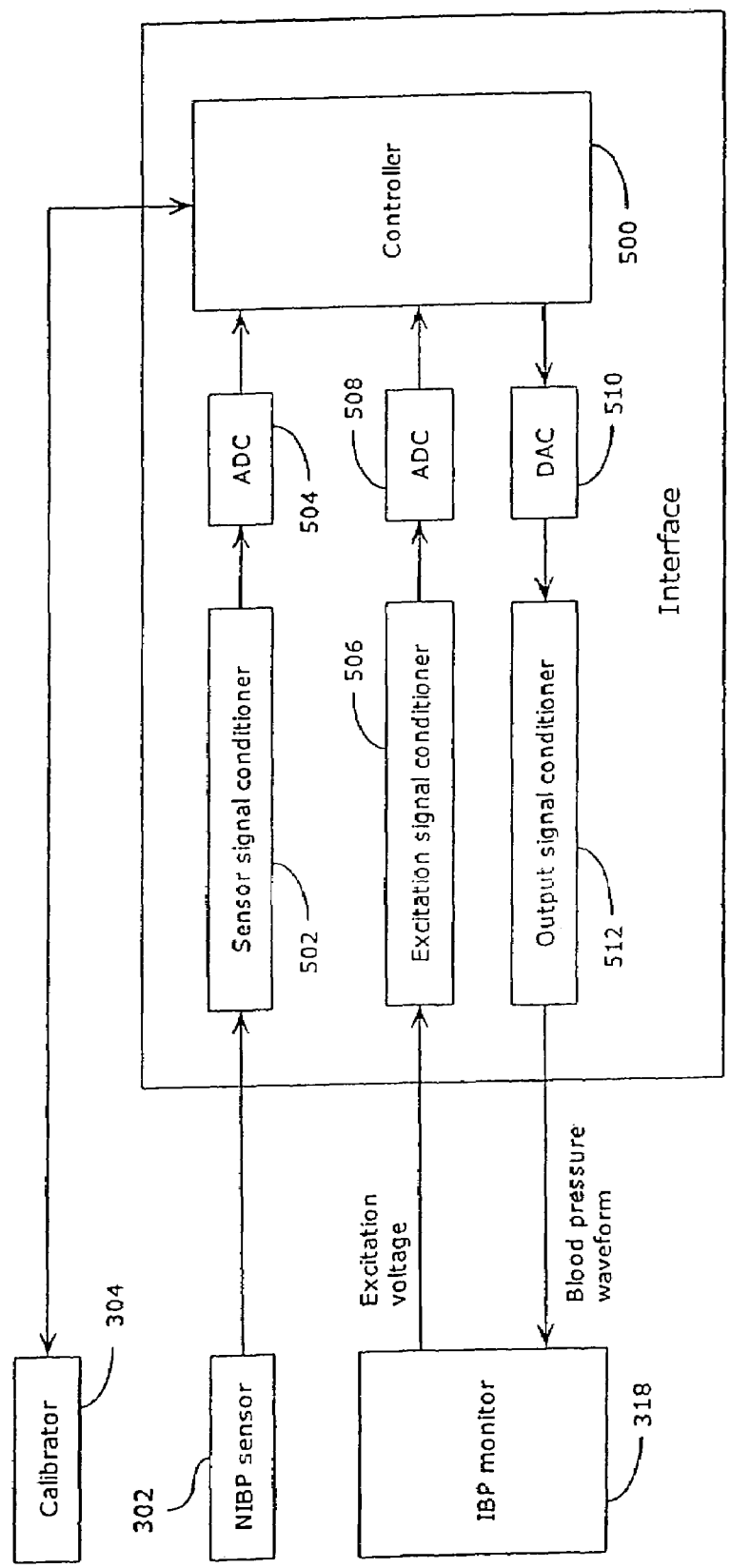
FIG. 9 is a block diagram for the NIBP monitoring systems of FIGS. 6, 7 and 8 showing the main elements of the interface and the general flow of signals.
Figure 10:
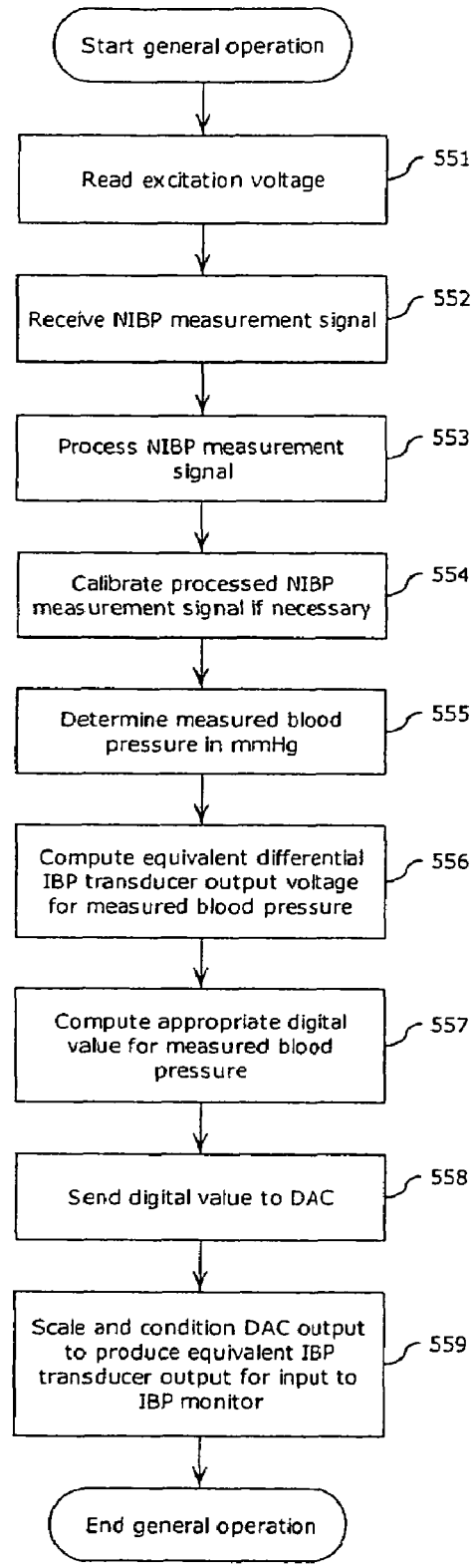
FIG. 10 is a flowchart illustrating the general operation of an interface designed in accordance with the present invention.

A block diagram of an NIBP monitoring system showing the main elements of an interface that uses the digital approach is presented in FIG. 9. The general operation of the interface involves the following steps, which are also illustrated in FIG. 10:

a) Step 551. The controller 500 reads the excitation voltage supplied by the IBP monitor 318, through an excitation signal conditioner 506 and an analog-to-digital converter (ADC) 508.

b) Step 552. The controller 500 receives the NIBP measurement signal from the NIBP sensor 302 through a sensor signal conditioner 502 and an ADC 504.

c) Step 553. The controller 500 processes the NIBP measurement signal.

d) Step 554. The controller 500 calibrates the processed NIBP measurement signal if necessary.

e) Step 555. The controller 500 determines the measured blood pressure in mmHg.

f) Step 556. The controller computes the equivalent differential IBP transducer output voltage for the measured blood pressure as the product of the transducer sensitivity, excitation voltage and measured blood pressure.

g) Step 557. The controller 500 computes an appropriate digital value that is proportional to this equivalent differential voltage.

h) Step 558. The controller 500 sends the digital value to a DAC 510.

i) Step 559. The output signal conditioner 512 scales and conditions the output voltage of the DAC 510 and outputs the equivalent IBP transducer output voltage for input to the IBP monitor 318.

Transducer Sensitivity

In order for the interface to be able to output the correct equivalent IBP transducer output signal to the IBP monitor for any measured blood pressure, the controller needs to know in advance the transducer sensitivity which the IBP monitor is configured to work with, as well as the excitation voltage supplied by the monitor. The excitation voltage is supplied by the IBP monitor and sensed by the controller through the excitation signal conditioner. However, the transducer sensitivity needs to be provided to the interface by the user, and it must be the same as that of the transducer sensitivity which the IBP monitor is configured to work with. This sensitivity is normally specified in the monitor's manual.

The interface can be designed in such a way that the transducer sensitivity is selectable by the user from among two or more sensitivities. Additionally, it can be designed to operate on a default sensitivity of 5 μV/V/mmHg, the most commonly used sensitivity, if no selection is made.

Digital Output for Measured Blood Pressure

For the same pressure measurement range and the same excitation voltage, a larger transducer sensitivity will give a larger range of output voltage. For example, for a pressure measurement range of 0 to 300 mmHg and an excitation voltage of 5 V, a 40 μV/V/mmHg transducer will give a full output voltage range of 60 mV (40 μVN/mmHg×5 V×300 mmHg), whereas a 5 μV/V/mmHg transducer will give an output voltage range of only 7.5 mV. If the DAC output voltage is to be scaled down by a factor of 100, the DAC must be able to output a voltage range of at least 6 V for the 40 μV/V/mmHg transducer and 0.75 V for the 5 μVN/mmHg transducer. This output voltage range can be expressed algebraicly:

$$V_{EXC} \times SENS \times (P_{MAX} - P_{MIN})$$

where $V_{EXC}$ is the root-mean-square (RMS) differential voltage across the excitation terminals, SENS is the transducer sensitivity which said IBP monitor is configured to work with, and PMAX and PMIN are respectively the maximum and minimum pressures which said interface is configured to work with.

If a DAC whose resolution in LSBN (least significant bits per volt) has been maximized for a 40 μVN/mmHg transducer sensitivity is used for a 5 μVN/mmHg sensitivity, the resolution of the DAC output voltage and hence the number of data points will be reduced, so that the blood pressure waveform becomes more steplike or less smooth than that obtained with a DAC whose resolution has been optimized for the 5 μVN/mmHg sensitivity. The more steplike a waveform is, the less it represents the actual waveform.

To improve the smoothness of the blood pressure waveform at the IBP monitor's end, the resolution of the DAC output voltage in LSBN should be maximized in such a way that the DAC is still able to produce the required DAC output voltage range, which, as indicated above, depends on the transducer sensitivity, excitation voltage, pressure measurement range, and the scaling factor for the DAC output voltage. All this can be accomplished by using a programmable DAC that allows its full-scale output voltage range to be configured by the controller, and by configuring the DAC for a full-scale output voltage range that is slightly larger than the required DAC output voltage range.

To further improve the smoothness of the blood pressure waveform that is displayed on the IBP monitor, the number of the digital values for the waveform can be increased by interpolation. A simple method is to perform linear interpolation between every two adjacent data points. Nonlinear interpolation methods such as quadratic interpolation and cubic spline interpolation can also be used.

Emulation of IBP Transducer Output Signal

For a full emulation of the output voltage level of the IBP transducer, the equivalent IBP transducer output voltage produced by the interface should be such that the voltage level of each of the two terminals for this equivalent voltage is the same as the level that would be produced at the corresponding output terminal of the transducer. Since the nominal midpoint voltage of the IBP transducer output signal is the same as the midpoint voltage between the excitation terminals, as mentioned above, this emulation can be accomplished by centering the differential output voltage about the midpoint voltage between the excitation terminals. In other words, the midpoint of the differential output voltage rides on the midpoint voltage between the excitation terminals, or the midpoint of the differential output voltage is offset with respect to the negative excitation terminal E− by half the voltage across the excitation terminals.

An approximate emulation of the IBP transducer output voltage level can be achieved by making one of the terminals for the differential output voltage take on the midpoint voltage between the excitation terminals. This approximate emulation is judged to be adequate because the differential output voltage is relatively small, being usually in the order of millivolts or tens of millivolts, compared to the midpoint voltage between the excitation terminals, which is of usually in the order of volts as measured with respect to the negative excitation terminal E−. Additionally, the circuitry for implementing this approximate emulation is likely to be simpler than that for the full emulation.

It is possible that without emulating this offset, the output voltage of the interface will still be accepted by most IBP monitors. For example, the HP1006B IBP module (Philips Medical Systems) has been shown in the laboratory to accept the output voltage from the interface when the negative output terminal S− is connected to the electrical ground of the interface. To be conservative, however, the voltage level of the output terminals should be emulated in case the IBP monitor uses this voltage level, among other characteristics, to check for proper functioning of the IBP transducer.

Input and Output Impedances

It is known that IBP monitors use the input impedance, output impedance, or both to detect the presence and absence of a transducer or whether the transducer is functioning properly, so these impedances should be emulated. Emulating these impedances will more accurately emulate the actual situation and help to reduce the chances of problems in communication between the interface and IBP monitor.

Circuitry for Interfacing with IBP Monitor

Figure 11:
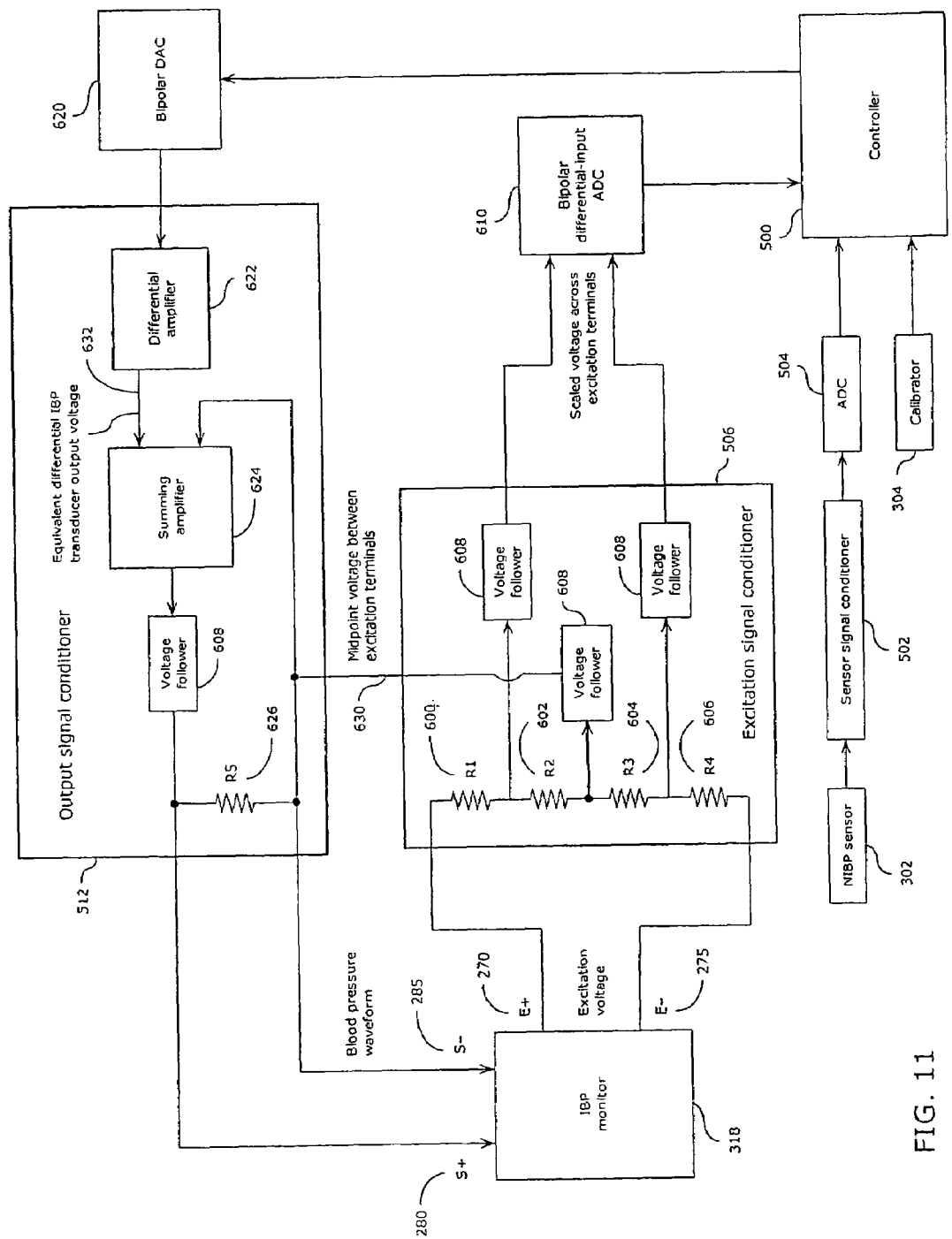
FIG. 11 is a block diagram of a proposed circuitry for interfacing with the IBP monitor.

An electrical schematic diagram of a proposed circuitry for interfacing with the IBP monitor is presented in FIG. 11. This circuitry provides for interfacing with the excitation and input terminals of the IBP monitor. It implements the approximate emulation discussed above. The circuitry includes unity-gain voltage followers 608 or buffers at various places to minimize loading and to ensure that any malfunctioning of the interface will not compromise the electrical safety and electrical performance of the IBP monitor.

Referring to FIG. 11, a voltage divider consisting of four resistors R1 600, R2 602, R3 604 and R4 606 of predetermined values and in series is placed across the excitation terminals such that R1 600 equals R4 606 and R2 602 equals R3 604. This means that the sum of R1 600 and R2 602 is equal to the sum of R3 604 and R4 606, so that the connection point between R2 602 and R3 604 gives the midpoint voltage 630 between the excitation terminals. The voltage across R2 602 and R3 604 represents a scaled version of the voltage across the excitation terminals, the scaling factor being given by the ratio (R2+R3)/(R1+R2+R3+R4). This scaled voltage is supplied to the input of a bipolar differential-input ADC 610, and the output of the ADC 610 is read by the controller 500. The bipolar ADC 610 accepts positive and negative input differential voltages. From this ratio, the controller 500 derives the voltage across the excitation terminals. The four resistors are selected in such a way that their sum is within the input impedance range of the IBP transducer which the IBP monitor is configured to work with—this is to emulate the input impedance of the transducer. Additionally, R2 602, R3 604 and the ADC 610 are configured in such a way that the voltage across R2 602 and R3 604 is within the full-scale input voltage range of the ADC 610.

From the voltage across the excitation terminals, transducer sensitivity and measured blood pressure, the controller 500 generates an appropriate digital value representing the measured blood pressure and sends the digital value to a bipolar DAC 620. The bipolar DAC 620 provides for positive and negative output voltages. The output voltage of the DAC 620 is scaled by means of a differential amplifier in such a way that that the output voltage is the same as the differential voltage that would have peen produced at the transducer output for the same transducer sensitivity, the same voltage across the excitation terminals, and the same measured blood pressure. This scaled differential voltage is then superimposed on the midpoint voltage 630 between the excitation terminals by means of a summing amplifier 624. The final output is supplied to the IBP monitor. A resistor R5 626 is placed across the output terminals such that R5 626 is within the output impedance range of the IBP transducer which the IBP monitor is configured to work with—this is to emulate the output impedance of he the transducer. Additionally, the DAC 620 and scaling factor for the DAC output voltage are selected in such a way that the DAC full-scale output voltage range includes the DAC output voltage range corresponding to the full range of the blood pressure which the interface is designed to measure.

Alternatives for various parts of the circuitry are available. First, the above circuitry uses the analog midpoint voltage 630 for the summing amplifier 624. One alternative method of obtaining the midpoint voltage is to have the controller read the midpoint excitation voltage through a signal conditioner and an ADC, generate a digital value and send the digital value to a DAC, and have a signal conditioner condition the DAC output voltage to the same level as that of the actual midpoint voltage. Another alternative method is to have the controller read the voltages at the excitation terminals E+ 270 and E− 275 and compute the midpoint excitation voltage, instead of reading the midpoint voltage directly. In both alternative methods, the circuitry can be designed to use an ADC with a fixed full-scale input voltage range, or me whose full-scale input voltage range can be configured through software or firmware in such a way that the measurement resolution in V/LSB is maximized to give a more accurate measurement of the excitation voltage.

Second, the voltage across the excitation terminals in the above circuitry is sensed through a voltage divider. This voltage can also be sensed through a differential amplifier or a combination of a voltage divider and a differential amplifier.

Third, the above circuitry uses a differential-input ADC to receive the scaled voltage across the excitation terminals and the controller to compute the actual differential voltage based on the scaling factor. One alternative method of obtaining the actual differential voltage is to use a single-ended-input ADC to receive the actual voltage of each of the excitation terminals E+ 270 and E− 275 or a scaled version of it, and have the controller compute the actual differential voltage.

Fourth, the midpoint voltage 630 between the excitation terminals in the above circuitry is sensed through a voltage divider. This midpoint voltage can also be sensed through a combination of a voltage divider and a differential amplifier.

Fifth, the above circuitry uses a differential amplifier 622 to scale the DAC output voltage. An alternative method to scale the DAC output is to use a voltage divider or a combination of a voltage divider and a differential amplifier.

It is recognized that the scaling factor for the DAC output voltage will differ from circuit assembly to circuit assembly because of variations in the components and at these variations will ultimately affect the accuracy of the voltage across the output terminals S+ 280 and S− 285. One way to resolve this problem is to determine the actual DAC output voltage scaling factor for every interface unit and then use the value for computational purposes in the software or firmware. Each interface unit will then have its own DAC output voltage scaling factor. This will help ensure that the correct output voltage s produced across the output terminals S+ 280 and S− 285.

It should be noted that the negative excitation terminal E− 275 should not be connected to the electrical ground of the interface, because E− 275 in general does not share the same electric potential as the electrical ground of the interface. Connecting them can lead to a ground loop that can damage both the interface and the IBP monitor, compromising the electrical safety and electrical performance of the devices. For comparison, when an IBP transducer is used with an IBP monitor, the E− terminal 275 of the transducer takes on whatever voltage is applied to that terminal by the IBP monitor 318. Using E− 275 as it is, that is, by not connecting it to the electrical ground of the interface, emulates this situation.

Calibration of NIBP Measurement Signal

For an NIBP monitor, calibration establishes the absolute reference blood pressure corresponding to the NIBP measurement signal. For an NIBP monitor that does not have built-in calibration capability, its NIBP measurement signal must be calibrated against blood pressure measurements made by another device. One such NIBP monitor is described in U.S. Pat. No. 6,443,906 entitled METHOD AND DEVICE FOR MONITORING BLOOD PRESSURE, the contents of which are incorporated herein by reference. An embodiment of this monitor comprises a tonometric NIBP sensor, a watch head that houses a microprocessor, and a strap. In this embodiment, the monitor is strapped to the wrist, with the NIBP sensor being placed over the radial artery to detect blood pressure in the artery. Wrist movement and changes in the properties of compressed tissue between the monitor and the wrist can cause the sensor to displace from its original position and the strap tension to change. This displacement and tension change will change the forces acting on the contact area between the sensor and the wrist. This change in forces will alter the NIBP measurement signal even if there has been no change in the arterial pressure.

For an NIBP monitoring system that uses the interface and the above tonometric NIBP sensor, calibration should be performed at the beginning of an NIBP measurement period and whenever there is reason to suspect that the alteration of the NIBP measurement signal might not have been caused by a change in the arterial pressure. The interface can be designed to activate a calibrator whenever calibration is required. For example, the interface can be designed to allow the user to initiate and abort a calibration, either by pressing a button on the interface or clicking on a button on the computer screen. It can also be designed to automatically initiate a calibration at predetermined intervals, at intervals that depend on deviations of the NIBP measurement signal from physiologically realistic signals, or at a combination of both groups of intervals, and to automatically abort the calibration when necessary.

It should be noted that the choice of a calibrator for an NIBP monitor that provides continuous beat-to-beat blood pressure measurement is not restricted to those that use an occlusive cuff. Any blood pressure measurement device that is capable of providing accurate blood pressure measurement can potentially be used as a calibrator.

Zeroing of IBP Transducer with IBP Monitor

The output voltage of an IBP transducer at zero mmHg is usually not zero. This output voltage is called the zero offset or zero balance. This offset voltage is sometimes augmented by hydrostatic pressure caused by a column of fluid above the level of the sensing area of the transducer. For accurate IBP measurement, the IBP transducer must be zeroed with the IBP monitor before monitoring begins. During the zeroing, the IBP, monitor effectively reads the total offset voltage and associates it with zero mmHg, or strictly speaking, zero gage pressure, and in doing so, establishes a zero-mmHg reference level for the IBP monitor.

The zeroing procedure for a fluid-filled pressure monitoring system requires the clinician to manually trigger the IBP monitor to perform the zeroing. It includes the following steps:

a) Prepare the IBP monitor to receive the transducer output voltage at zero mmHg.

b) Position the zeroing port of the IBP transducer so that it is at the patient's mid-heart level.

c) Turn the handle of the zeroing stopcock OFF to the patient and loosen or remove the deadender cap on the zeroing side port. This step blocks the transducer from the patient's intra-arterial pressure and opens the transducer to the atmosphere. Some fluid will flow out of the side port as a result.

d) Zero the transducer with the IBP monitor by pressing the appropriate key or button on the IBP monitor. This zeroing has to be activated manually because there is no automated feedback to check whether or not the fluid-filled system is ready to be zeroed.

e) Turn the stopcock handle OFF to the zeroing side port (closing the port to atmosphere) to re-admit patient's pressure. The patient's intra-arterial pressure waveform will now show up on the IBP monitor.

f) Tighten the deadender cap to close the side port.

Zeroing of Interface with IBP Monitor

For an NIBP monitoring system that uses the interface, the tonometric NIBP sensor as mentioned above, and a calibrator that uses an occlusive cuff, the initial zeroing procedure could include the following steps:

a) Prepare the IBP monitor to receive the transducer output voltage at zero mmHg.

b) Calibrate the NIBP measurement signal using the calibrator, with the applied cuff at the patient's mid-heart level. From the reference blood pressures measured by the calibrator and the NIBP measurement signal received, the controller will establish a calibration relationship that relates the NIBP measurement signal to blood pressure in mmHg. Because an IBP transducer in general does not require any calibration when it is in use, this step can be considered to be only partially equivalent to positioning the zeroing port of the BP transducer at the patient's mid-heart level, as described in step (b) of the transducer zeroing procedure.

c) Send a zero-mmHg signal to the IBP monitor, by sending to the DAC a digital value corresponding to zero mmHg. The sending of this signal can be initiated automatically by the interface, or by the user pressing a button on the interface or on the computer screen. This step is equivalent to opening the IBP transducer to the atmosphere, as described in step (c) of the transducer zeroing procedure. This digital value can be a zero or a non-zero value, as long as the zero-mmHg signal that is sent to the IBP monitor is within the range corresponding to the range of the zero balance for which the IBP monitor is configured to work with. Although the AAMI standard stipulates a zero balance within ±75 mmHg, as mentioned above, most IBP monitors are designed to accept a larger range of zero balance.

d) Zero the interface with the IBP monitor, by pressing the appropriate key or button on the IBP monitor. This step is equivalent to zeroing the IBP transducer, as described in step (d) of the transducer zeroing procedure.

e) Send equivalent IBP transducer output voltage to the IBP monitor by pressing a button on the interface or clicking on a button on the computer screen. The interface will send the equivalent IBP transducer output voltage to the IBP monitor. This step is equivalent to turning the stopcock handle of the BP transducer OFF to the zeroing side port to re-admit the patient's pressure, as described in step (e) of the transducer zeroing procedure.

It should be noted that the above NIBP monitoring system has no equivalent step for step (f) of the transducer zeroing procedure.

The above procedure indicates that zeroing is performed and calibration. Calibration can actually be performed before the zeroing, meaning the above steps for the NIBP monitoring system can proceed in the order of a, c, d, b, and e. Any subsequent re-calibration can proceed without any zeroing unless it is required for other reasons. If no calibration is required, step (b) can be removed. In any case, zeroing and calibration should be performed only after sufficient time has been given for the NIBP monitoring system to warm up after its initial power-up.

If a re-calibration is performed while the equivalent IBP transducer output signal is still being sent to the IBP monitor, the blood pressure waveform will appear distorted if the occlusive cuff of the calibrator is applied to the same arm as the NIBP sensor. This is because the occlusion of the brachial artery by the cuff will alter the normal transmission of arterial pressure to the radial artery. Although the distorted waveform can actually be used to indicate that calibration is in progress, it may inadvertently confuse the clinician. The software or firmware of the NIBP monitoring system can be designed to provide the option of temporarily not displaying the distorted waveform on the IBP monitor whenever calibration is in progress. This can be achieved by sending a zero-mmHg signal to the IBP monitor to display a zero-mmHg line and at the same time displaying a "calibration in progress" message on the monitor to inform the clinician.

If the calibrator cuff is applied to the opposite arm, the blood pressure waveform will not be distorted during calibration, so it will not be necessary to prevent the waveform from being displayed on the IBP monitor unless there is reason to do so. This means that the waveform can continue to be displayed on the IBP monitor whether or not calibration is in progress. However, because the clinician may apply the occlusive cuff to the same arm or a different arm, it may be advisable to design the interface in such a way that a zero-mmHg signal is always sent to the IBP monitor when calibration is in progress.

Depending on the stability of the interface output signal at zero mmHg, it may be necessary to perform zeroing at regular or preprogrammed intervals. The zeroing can be followed, though not necessarily, by a calibration. For example, if the ambient temperature fluctuates too much after the NIBP monitoring system has been zeroed and calibrated for the first time at the start of a measurement period, a re-calibration followed by a re-zeroing is advisable. In general, however, a calibration of the NIBP monitoring system, whether initiated by the user or automatically by the system, need not always be followed by a zeroing unless there is reason to do so.

To ensure that no unwanted signal is displayed on the IBP monitor, the interface can be configured in such a way that by default, a zero-mmHg signal is always automatically sent to the IBP monitor whenever the interface is powered up. Additionally, the buttons that are used by the user to send a zero-mmHg signal and the equivalent IBP transducer output voltage to the IBP monitor can be designed to be the same button that toggles between the two functions.

Operating Procedure for Interface

Figure 12:
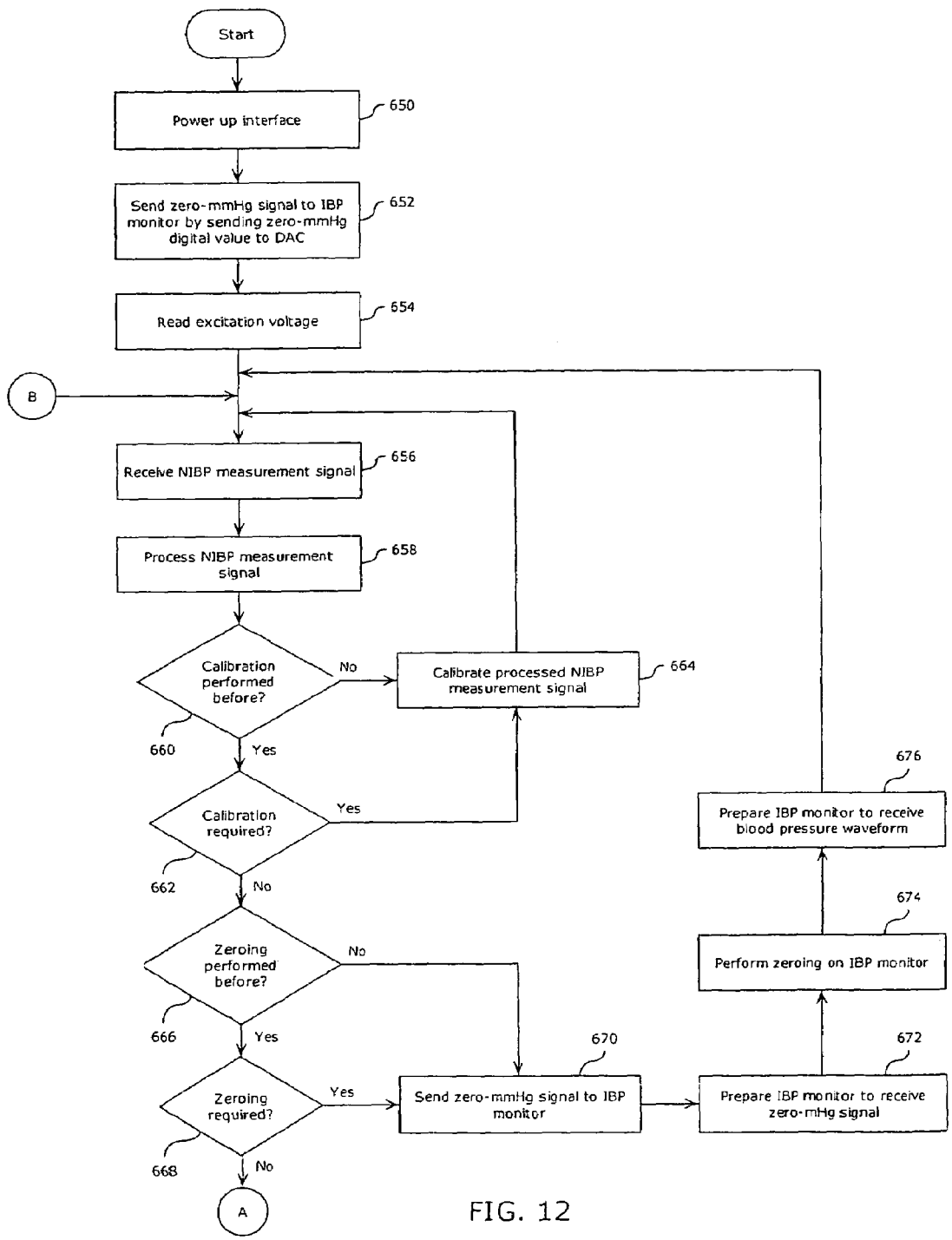
FIG. 12 is a flowchart illustrating an operating procedure for an interface designed in accordance with the present invention.
Figure 13:
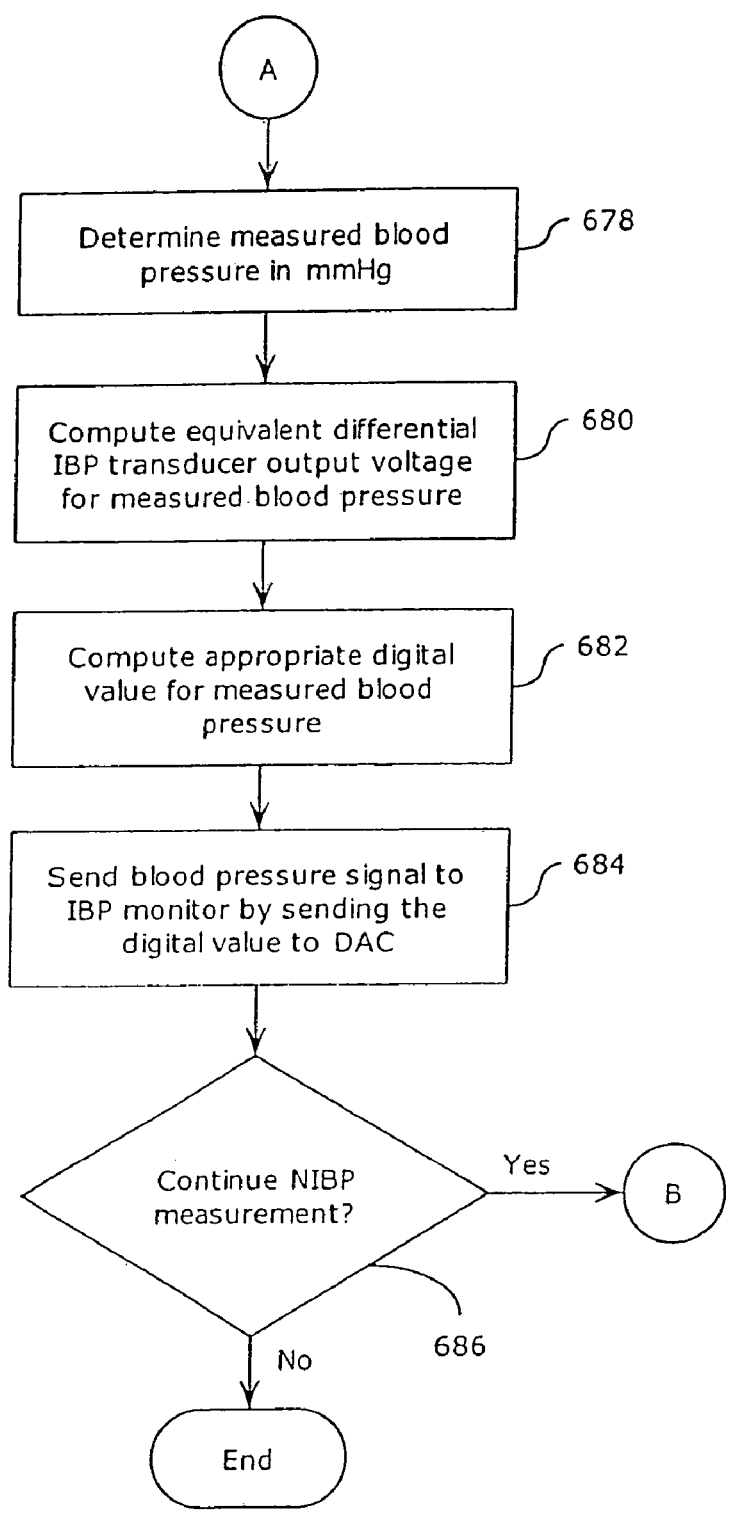
FIG. 13 is a continuation of the flowchart of FIG. 12.

A flowchart for an operating procedure that includes calibration and zeroing is illustrated in FIGS. 12 and 13. It involves the following:

a) Upon power-up of the interface in step 650, a zero-mmHg signal is sent by the interface to the IBP monitor through step 652.
b) The excitation voltage is read through step 654.
c) The NIBP measurement signal is received through step 656 and processed through step 658.
d) If calibration has not been performed before or if it is required for other reasons, it is performed through step 664, after which the controller returns to step 656 to continue receiving the NIBP measurement signal.
e) If zeroing has not been performed before or if it is required for other reasons, it is performed through steps 670, 672, 674 and 676, after which the controller returns to step 656 to continue receiving the NIBP measurement signal.
f) If calibration and zeroing is not required, the measured blood pressure is determined through step 678.
g) The equivalent differential IBP transducer output voltage for the measured blood pressure is computed through step 680.
h) The appropriate digital value for this differential voltage is computed through step 682.
i) The computed digital value is send to the DAC through step 684.
j) If continuation of the NIBP measurement is required, the controller returns to step 656 to continue receiving the NIBP measurement signal.
k) If continuation of the NIBP measurement is not required, the procedure ends.

Input, Intermediate and Output Signals

Figure 14:
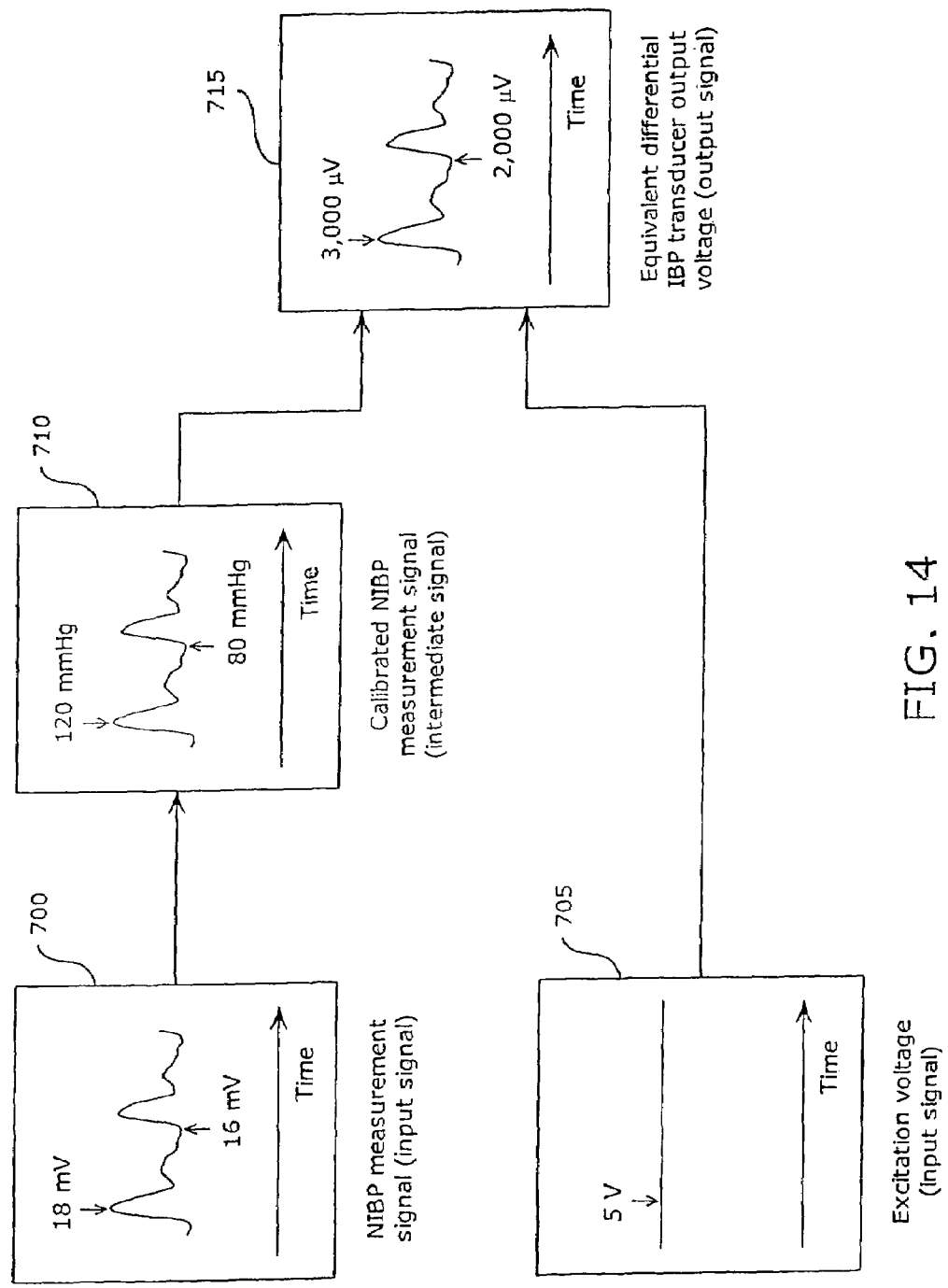
FIG. 14 is an illustration of the input, intermediate and output signals of an interface designed in accordance with the present invention

An illustration of the input, intermediate and output signals for an interface using the tonometric NIBP sensor mentioned above and a transducer sensitivity of 5 µV/V/mmHg is presented in FIG. 14. The NIBP measurement signal 700 and excitation voltage 705 are the input signals. The calibrated NIBP measurement signal 710 is the intermediate signal, which is generated by the controller. The equivalent differential IBP transducer output voltage 715 is the same as the voltage across the output terminals S+ 280 and S− 285 of the interface (FIG. 11).

FIG. 14 shows a calibrated signal with a systolic pressure of 120 mmHg and a diastolic pressure of 80 mmHg for the first beat of the waveform. The corresponding equivalent differential IBP transducer output voltage for the systolic pressure is given by (120 mmHg×5 V×5 µV/V/mmHg), or 3,000 µV. Similarly, the corresponding equivalent differential IBP transducer output voltage for the diastolic pressure is given by (80 mmHg×5 V×5 V/V/mmHg), or 2,000 µV. These output voltages are indicated in the output signal block 715.

The invention claimed is:

1. An interface configured to connect between a noninvasive blood pressure (NIBP) sensor and an invasive blood pressure (IBP) monitor comprising:
    a first input configured to receive a measurement signal indicative of a NIBP of a subject from said NIBP sensor;
    a second input configured to receive a transducer excitation signal provided by said IBP monitor;
    at least one processor(s) configured to receive said measurement signal and said excitation signal and emulate an output signal indicative of an IBP of said subject according to predetermined instructions; and
    an output configured to provide said output signal in a form suitable for input to said IBP monitor;

wherein said processor(s) is further configured to supply a zeroing signal to said output when calibration of said measurement signal is in progress or when said measurement signal is distorted.

2. An interface as claimed in claim 1 wherein the sending of said zeroing signal and said output signal can be initiated and aborted by a user.

3. An interface as claimed in claim 2 wherein the sending of said zeroing signal and said output signal can be alternated by a user.

4. An interface as claimed in claim 1 wherein said zeroing signal is supplied to said output upon power-up of said interface.

5. An interface as claimed in claim 1 wherein said zeroing signal is always supplied to said output whenever no other signal is supplied to said output.

6. An interface as claimed in claim 1 wherein the output signal for said zeroing signal is within ±75 mmHg.

* * * * *